US011236153B2

United States Patent
Grakoui et al.

(10) Patent No.: US 11,236,153 B2
(45) Date of Patent: Feb. 1, 2022

(54) COMPOSITIONS AND METHODS FOR IDENTIFYING AND SORTING ANTIGEN-SPECIFIC B CELLS

(71) Applicants: Emory University, Atlanta, GA (US); Rutgers, The State University of New Jersey, New Brunswick, NJ (US)

(72) Inventors: Arash Grakoui, Decatur, GA (US); Joseph Marcotrigiano, New Brunswick, NJ (US)

(73) Assignees: Emory University, Atlanta, GA (US); Rutgers, the State University of New Jersey, New Brunswick, NJ (US)

( * ) Notice: Subject to any disclaimer, the term of this patent is extended or adjusted under 35 U.S.C. 154(b) by 91 days.

(21) Appl. No.: 16/335,891

(22) PCT Filed: Sep. 22, 2017

(86) PCT No.: PCT/US2017/052882
§ 371 (c)(1),
(2) Date: Mar. 22, 2019

(87) PCT Pub. No.: WO2018/057843
PCT Pub. Date: Mar. 29, 2018

(65) Prior Publication Data
US 2020/0181242 A1 Jun. 11, 2020

Related U.S. Application Data

(60) Provisional application No. 62/398,901, filed on Sep. 23, 2016.

(51) Int. Cl.
| | | |
|---|---|---|
| *A61K 39/00* | (2006.01) |
| *A61K 39/21* | (2006.01) |
| *C12N 7/00* | (2006.01) |
| *A61K 39/12* | (2006.01) |
| *C12N 15/00* | (2006.01) |
| *C07K 16/10* | (2006.01) |
| *C12N 15/10* | (2006.01) |
| *C12Q 1/686* | (2018.01) |

(52) U.S. Cl.
CPC ........ *C07K 16/109* (2013.01); *C07K 16/1063* (2013.01); *C12N 15/1006* (2013.01); *C12Q 1/686* (2013.01); *C12N 2740/16122* (2013.01); *C12N 2770/24222* (2013.01)

(58) Field of Classification Search
CPC .......... A61P 31/18; A61P 31/12; A61P 37/02; A61P 37/04; A61K 2039/54
See application file for complete search history.

(56) References Cited

U.S. PATENT DOCUMENTS

| | | | |
|---|---|---|---|
| 2008/0138894 A1 | 6/2008 | Maertens | |
| 2010/0284967 A1* | 11/2010 | Dewhurst | .......... C12N 15/1037 424/85.4 |
| 2014/0272932 A1* | 9/2014 | Muerhoff | ............. C07K 14/005 435/5 |

OTHER PUBLICATIONS

Rodriguez et al. "Structural properties of the ectodomain of hepatitis C virus E2 envelope protein" Virus Res., 2009, 139(1):91-99.*
Boivert et al. Novel E2 Glycoprotein Tetramer Detects Hepatitis C Virus-Specific Memory B Cells, The Journal of Immunology, 2016, 197: 4848-4858.
Fairhead et al. Site-specific biotinylation of purified proteins using BirA, Methods Mol Biol. 2015, 1266: 171-184.
Franz et al. Ex vivo characterization and isolation of rare memory B cells with antigen tetramers, Blood, 2011, 118(2):348-357.
Hamilton et al. General Approach for Tetramer-Based Identification of Autoantigen-Reactive B Cells Characterization of La- and snRNP-Reactive B Cells in Autoimmune BXD2 Mice, The Journal of Immunology, 2015, 194: 5022-5034.
Kahn et al. Structure of the Core Ectodomain of the Hepatitis C Virus Envelope Glycoprotein 2, Nature. 2014, 509(7500): 381-384.
Morris et al. Isolation of a Human Anti-HIV gp41 Membrane Proximal Region Neutralizing Antibody by Antigen-Specific Single B Cell Sorting, PLoS ONE, 2011, 6(9): e23532.
Ritchie et al. Analysis of HIV-1 Gag Protein Interactions via Biotin Ligase Tagging, J Virol, 2015 89:3988-4001.
Rodriguez et al., Structural properties of the ectodomain of hepatitis C virus E2 envelope protein, Virus Research 139 (2009) 91-99.
Smith et al. Detection and Enrichment of Rare Antigen-specific B Cells for Analysis of Phenotype and Function, J Vis Exp, 2017 (120): 55382.
Wink et al. High-content imaging-based BAC-GFP toxicity pathway reporters to assess chemical adversity liabilities, Arch Toxicol (2017) 91:1367-1383.

* cited by examiner

*Primary Examiner* — Barry A Chestnut
(74) *Attorney, Agent, or Firm* — Emory Patent Group

(57) ABSTRACT

The present disclosure relates to constructs useful in expressing biotinylated monomers and tetramers produced from these monomers. Specifically, the disclosure provides a construct useful in expressing biotinylated antigen monomers, said construct comprising a viral protein of an ectodomain of Hepatitis C Virus (HCV) envelope glycoprotein E2 or Human Immunodeficiency Virus (HIV) gp140. Further disclosed are methods for production and use of these tetramers in identifying and isolating antigen specific B cells and cloning antibodies thereto.

10 Claims, 8 Drawing Sheets
Specification includes a Sequence Listing.

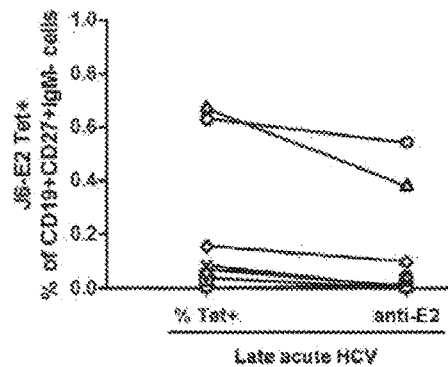
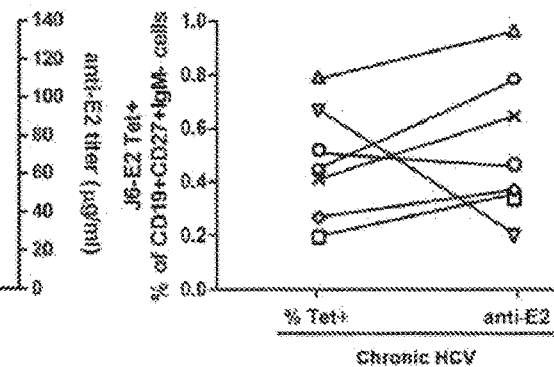
FIG. 4C
FIG. 4D
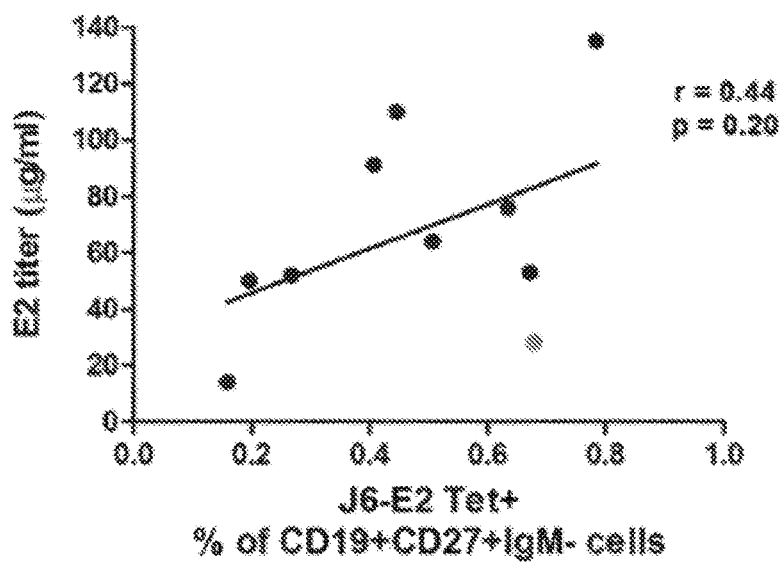
FIG. 4E

SEQUENCE LISTING

```
<160> NUMBER OF SEQ ID NOS: 4

<210> SEQ ID NO 1
<211> LENGTH: 28
<212> TYPE: PRT
<213> ORGANISM: Artificial
<220> FEATURE:
<223> OTHER INFORMATION: Synthetic

<400> SEQUENCE: 1

Met Asn Ile Lys Gly Ser Pro Trp Lys Gly Ser Leu Leu Leu Leu Leu
1               5                   10                  15

Val Ser Asn Leu Leu Leu Cys Gln Ser Val Ala Pro
            20                  25

<210> SEQ ID NO 2
<211> LENGTH: 15
<212> TYPE: PRT
<213> ORGANISM: Artificial
<220> FEATURE:
<223> OTHER INFORMATION: Synthetic

<400> SEQUENCE: 2

Gly Leu Asn Asp Ile Phe Glu Ala Gln Lys Ile Glu Trp His Glu
1               5                   10                  15

<210> SEQ ID NO 3
```

```
<211> LENGTH: 8
<212> TYPE: PRT
<213> ORGANISM: Artificial
<220> FEATURE:
<223> OTHER INFORMATION: Synthetic

<400> SEQUENCE: 3

Leu Glu Val Leu Phe Gln Gly Pro
1               5

<210> SEQ ID NO 4
<211> LENGTH: 280
<212> TYPE: PRT
<213> ORGANISM: Artificial
<220> FEATURE:
<223> OTHER INFORMATION: Synthetic

<400> SEQUENCE: 4

Thr His Thr Val Gly Gly Ser Ala Ala Gln Thr Thr Gly Arg Leu Thr
1               5                   10                  15

Ser Leu Phe Asp Met Gly Pro Arg Gln Lys Ile Gln Leu Val Asn Thr
            20                  25                  30

Asn Gly Ser Trp His Ile Asn Arg Thr Ala Leu Asn Cys Asn Asp Ser
        35                  40                  45

Leu His Thr Gly Phe Ile Ala Ser Leu Phe Tyr Thr His Ser Phe Asn
    50                  55                  60

Ser Ser Gly Cys Pro Glu Arg Met Ser Ala Cys Arg Ser Ile Glu Ala
65                  70                  75                  80

Phe Arg Val Gly Trp Gly Ala Leu Gln Tyr Glu Asp Asn Val Thr Asn
                85                  90                  95

Pro Glu Asp Met Arg Pro Tyr Cys Trp His Tyr Pro Pro Arg Gln Cys
            100                 105                 110

Gly Val Val Ser Ala Lys Thr Val Cys Gly Pro Val Tyr Cys Phe Thr
        115                 120                 125

Pro Ser Pro Val Val Val Gly Thr Thr Asp Arg Leu Gly Ala Pro Thr
    130                 135                 140

Tyr Thr Trp Gly Glu Asn Glu Thr Asp Val Phe Leu Leu Asn Ser Thr
145                 150                 155                 160

Arg Pro Pro Leu Gly Ser Trp Phe Gly Cys Thr Trp Met Asn Ser Ser
                165                 170                 175

Gly Tyr Thr Lys Thr Cys Gly Ala Pro Pro Cys Arg Thr Arg Ala Asp
            180                 185                 190

Phe Asn Ala Ser Thr Asp Leu Leu Cys Pro Thr Asp Cys Phe Arg Lys
        195                 200                 205

His Pro Asp Thr Thr Tyr Leu Lys Cys Gly Ser Gly Pro Trp Leu Thr
    210                 215                 220

Pro Arg Cys Leu Ile Asp Tyr Pro Tyr Arg Leu Trp His Tyr Pro Cys
225                 230                 235                 240

Thr Val Asn Tyr Thr Ile Phe Lys Ile Arg Met Tyr Val Gly Gly Val
                245                 250                 255

Glu His Arg Leu Thr Ala Ala Cys Asn Phe Thr Arg Gly Asp Arg Cys
            260                 265                 270

Asn Leu Glu Asp Arg Asp Arg Ser
        275                 280
```

COMPOSITIONS AND METHODS FOR IDENTIFYING AND SORTING ANTIGEN-SPECIFIC B CELLS

CROSS-REFERENCE TO RELATED APPLICATIONS

This application is the National Stage of International Application No. PCT/US2017/052882 filed Sep. 22, 2017, which claims the benefit of U.S. Provisional Application No. 62/398,901 filed Sep. 23, 2016. The entirety of each of these applications is hereby incorporated by reference for all purposes.

STATEMENT REGARDING FEDERALLY SPONSORED RESEARCH OR DEVELOPMENT

This invention was made with government support under RO1 AI070101 awarded by the NIH. The government has certain rights in the invention.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy, and is hereby incorporated by reference into the specification. The name of the text file containing the Sequence Listing is 17017US_ST25.txt. The text file is 4 KB, was created on Mar. 21, 2019, and is being submitted electronically via EFS-Web.

BACKGROUND

Hepatitis C virus (HCV) infection remains a global public health problem. In the United States, infection rates have increased steadily over the past decade primarily due to injection drug use among adolescents and young adults (Suryaprasad et al. Clin Infect Dis 2014, 59:1411-1419). Although direct acting antivirals (DAA) are generally safe and most persistent infections are cured within 2-3 months of therapy (Schinazi et al. Liver Int 2014, 34 Suppl 1: 69-78), their high cost, limited availability and the asymptomatic nature of most infections remain important challenges. Furthermore, successful treatment of chronic HCV infection with DAAs does not prevent reinfection, which is a recurrent problem for the high risk population (Simmons et al. Clinical infectious diseases: an official publication of the Infectious Diseases Society of America 2016, 62: 683-694).

The development of a prophylactic vaccine to inhibit HCV transmission is still a major goal. An interesting candidate, currently in phase 2 clinical trials is based on the prime-boost strategy with the first immunization using chimpanzee adenovirus together with a boost using a modified vaccinia Ankara (MVA) vector both expressing the non-structural region of HCV genome. In a phase 1 clinical study, this vaccine was well tolerated and induced a strong T cell response (Swadling et al. Science translational medicine 2014, 6: 261ra153). However, an optimal vaccine would combine both T and B cell responses (Cashman et al. Frontiers in immunology 2014 5: 550). It was shown that immunization with recombinant HCV E1E2 glycoproteins elicited a cross-reactive neutralizing antibody response in humans (Law et al. PloS one 2013, 8: e59776).

Published U.S. Patent Application No. 2015/0368668 discloses methods for preparing HCV E2 ectodomain polypeptides, methods of preparing HCV vaccines, methods of preparing HCV cell entrance inhibitors and models which can be used to develop HCV vaccines and new inhibitors.

Seroconversion to HCV envelope glycoproteins 1 (E1) and 2 (E2) usually occurs several weeks after infection, regardless of whether the virus is cleared or persists (Logvinoff et al. Proceedings of the National Academy of Sciences of the United States of America 2004 101: 10149-10154; Netski et al. Clinical infectious diseases an official publication of the Infectious Diseases Society of America 2005, 41: 667-675). The neutralizing effect of anti-HCV antibodies was demonstrated in both the chimpanzees (Farci et al. Proceedings of the National Academy of Sciences of the United States of America 1996, 93: 15394-15399; Morin et al. PLoS pathogens 2012 8: e1002895) and humanized mouse models of HCV infection (Law et al. Nature medicine 2008 14: 25-27; Vanwolleghem et al. Hepatology 2008, 47: 1846-1855). In these studies, incubation of an HCV inoculum with anti-HCV antibodies prevented infection, as did a passive transfer of the antibodies before the challenge (Farci et al. supra; Morin et al. supra; Law et al., supra; Vanwolleghem et al. supra). In humans, broadly neutralizing antibodies was shown to have developed more rapidly and to higher titers in individuals with an acute resolving infection as compared to those with persisting infection (Dowd et al. Gastroenterology 2009, 136: 2377-2386; Osburn et al. Hepatology 2014, 59: 2140-2151; Pestka et al. Proceedings of the National Academy of Sciences of the United States of America 2007 104: 6025-6030; Raghuraman et al. The Journal of infectious diseases 2012, 205: 763-771; Esteban-Riesco et al. 2013, Virology 444: 90-99).

In the context of reinfection, a subsequent exposure to HCV led to the development of cross-reactive antibodies, suggesting an improved humoral response (Osburn et al. Gastroenterology 2010, 138: 315-324).

However, some reports suggest that the infection can be resolved in the absence of any detectable HCV-specific antibody responses in both chimpanzees and humans (Thimme et al. Proc Natl Acad Sci USA 2002, 99: 15661-15668; Post et al. The Journal of infectious diseases 2004 189: 1846-1855; Meyer et al. Virology journal 2007, 4: 58). In those studies, HCV viral loads were low, and HCV-specific T cell responses were detected suggesting that a very transient viremia might not be enough to prime HCV-specific antibody responses. Furthermore, examining immune responses in a cohort of women who spontaneously resolved a single source outbreak of HCV demonstrated that circulating HCV-specific antibodies were undetectable in many subjects 18-20 years after recovery (Takaki et al. Nature medicine 2000, 6: 578-582). These opposing results have led to confusion regarding the contribution of HCV-specific antibodies to clearance of infection and highlight the need to obtain a better insight of the nature of humoral immune response during acute HCV infection.

There are currently no reagents available to directly examine HCV-specific B cells. Antigen-specific IgG-secreting memory B cell frequencies can be evaluated by bulk B cell stimulation coupled with enzyme-linked ImmunoSpot (ELISPOT) assays (Sugalski et al. J Immunol 2010, 185: 3019-3027). Although informative, this method does not allow for direct characterization or recovery of the HCV-specific B cells for downstream analyses. Alternatively, identification of antigen-specific B cells is possible using tetramers generated from biotinylated antigen coupled with fluorescently labeled streptavidin. In order to better evaluate the potential of a viral vaccine eliciting an effective humoral response, better insight into the development of a protective B cell response during acute viral infection is needed.

Hamilton et al. report a general approach for tetramer-based identification of autoantigen-reactive B cells. J Immunol 2015, 194(10):5022-34.

Franz et al. report ex vivo characterization and isolation of rare memory B cells with antigen tetramers. Blood 2011, 118(2): 348-357.

Morris et al. report the isolation of a human anti-HIV gp41 membrane proximal region neutralizing antibody by antigen-specific single B cell sorting. PloS one 2011, 6:e23532.

Fairhead et al. report enzymatic biotinylation with E. coli biotin ligase (BirA). Methods Mol Biol 2015, 1266: 171-184.

References cited herein are not an admission of prior art.

SUMMARY

The present disclosure relates to constructs useful in expressing biotinylated monomers and tetramers produced from these monomers. The present disclosure also relates to methods for production and use of these tetramers in identifying and isolating antigen specific B cells and cloning antibodies thereto.

An aspect of the present disclosure relates to a construct useful in expressing biotinylated antigen monomers. The construct comprises a viral protein or functional fragment thereof cloned downstream of a signal sequence which promotes targeting and trafficking through a secretory pathway. The monomer further comprises a biotinylation site inserted downstream or upstream of the viral protein. In addition, the construct may comprise a cleavage site, a tag for affinity purification and/or a reporter gene inserted downstream of the viral protein or functional fragment thereof.

Another aspect of the present disclosure relates to a tetramer comprising a plurality of biotinylated antigen monomers. Another aspect of the present disclosure relates to methods for use of the tetramers in identifying and isolating antigen specific B cells and cloning antibodies thereto.

In certain embodiments, this disclosure relates to a vector comprising a nucleic acid segment encoding a fusion protein comprising a signal sequence N-terminal to a viral antigen sequence followed by a C-terminal biotinylation site in operable combination with a heterologous promotor. In certain embodiments, the fusion protein further comprises a cleavage site and a tag for affinity purification C-terminal to the biotinylation site. In certain embodiments, the vector further comprises a reporter gene in operable combination with an internal ribosome entry site sequence wherein the reporter gene is downstream from the segment of nucleic acid encoding the fusion protein.

BRIEF DESCRIPTION OF THE DRAWINGS

FIG. 4C shows data when plasma anti-E2 IgG titers were measured by ELISA and compared with the tetramer frequencies for the late acute HCV time point.

FIG. 4D shows data in chronic HCV time point (n=7).

FIG. 4E shows data indicating a correlation between anti-E2 titers and J6-E2 tetramer positive frequencies from class-switched memory B cells.

DETAILED DESCRIPTION

Figure 1A:
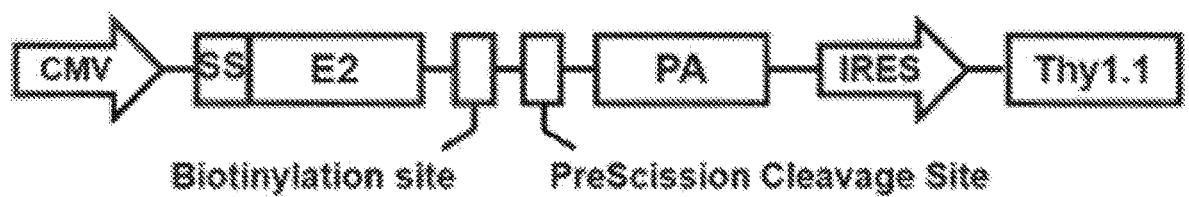
FIG. 1A shows schematic diagram of the E2-protein A (E2-PA) expression cassette in the pCMJJ4 vector. The ectodomain of E2 (aa 384-664; J6 [genotype 2a]) was cloned downstream of prolactin signal sequence (SS) to promote targeting and trafficking through the secretory pathway. A BSP85 sequence was inserted downstream for site-specific monobiotinylation followed by a preScission cleavage site and a proteinA (PA) tag for affinity purification and elution of purified E2-biotin monomer. The reporter gene Thy1.1 expression was cloned under the control of an internal ribosome entry site.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Monomer constructs of the present disclosure comprise a viral protein or functional fragment thereof. In one nonlimiting embodiment, the viral protein is a viral glycoprotein.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise.

As used herein, the term "nucleic acid" is intended to mean a ribonucleic or deoxyribonucleic acid or analog thereof, including a nucleic acid analyte presented in any context; for example, a probe, target or primer. A nucleic acid can include native or non-native bases. In this regard, a native deoxyribonucleic acid can have one or more bases selected from the group consisting of adenine, thymine, cytosine or guanine and a ribonucleic acid can have one or more bases selected from the group consisting of uracil, adenine, cytosine or guanine. It will be understood that a deoxyribonucleic acid used in the methods or compositions set forth herein can include uracil bases and a ribonucleic acid can include a thymine base.

In certain embodiments, the present disclosure relates to monomer constructs, tetramers, functional fragments thereof, and methods for use of the tetramers in understanding the development of a protective B cell response during viral infections and evaluating the potential of viral vaccines eliciting an effective humoral response. By "functional fragment thereof," it is meant a portion of the viral protein sufficient to produce a tetramer capable of recognizing B cells specific to the viral protein.

In certain embodiments, the monomer construct comprises a biotinylation site inserted upstream or downstream of the viral protein or functional fragment thereof. The monomer construct may further comprise a signal sequence upstream from the viral protein or functional fragment thereof. The signal sequence promotes targeting and trafficking through a secretory pathway. Multiple signal sequences are known to the skilled artisan and could be used in the present disclosure upon reading this disclosure. Non-limiting examples of signal sequence useful in the construct of the present disclosure the prolactin signal sequence and the signal sequence of the E2 protein.

The monomer construct may further comprise a cleavage site inserted downstream of the viral protein or functional fragment thereof and the biotinylation site. Multiple cleavage sites are known to the skilled artisan and could be used in the present disclosure upon reading this disclosure. A nonlimiting example of a cleavage site useful in the monomer constructs of the present disclosure is a PreScission™ cleavage.

The monomer construct may further comprises a tag for affinity purification inserted downstream of the viral protein or functional fragment thereof and the biotinylation site. Multiple affinity purification tags are known to the skilled artisan and could be used in the present disclosure upon reading this disclosure. A nonlimiting example of a tag for affinity purification useful in the monomer constructs of the present disclosure is Protein A tag.

In addition, the monomer construct may further comprise a reporter gene inserted downstream of the viral protein or functional fragment thereof and the biotinylation site. Multiple reporter genes are known to the skilled artisan and could be used in the present disclosure upon reading this disclosure. A nonlimiting example of a reporter gene useful in the monomer constructs of the present disclosure is the reporter gene Thy1.1 under the control of an internal ribosome entry site (IRES).

The biotinylated monomers of the construct are produced by introduction into a cell line. Multiple cell lines are known to the skilled artisan and could be used in the present disclosure upon reading this disclosure. A nonlimiting example of a cell line useful in production of the monomers is lentivirus-transduced Human Embryonic Kidney 293 cells.

Tetramers of the present disclosure can then be produced by incubating the monomer with fluorescence (APC) labeled streptavidin.

In certain embodiments, the signal sequence is the human prolactin signal sequence MNIKGSPWKGSLLLLL-VSNLLLCQSVAP (SEQ ID NO: 1). In certain embodiments, the biotinylation site comprises the sequence GLN-DIFEAQKIEWHE (SEQ ID NO: 2). In certain embodiments, the cleavage site is the human rhinovirus 3C protease site LEVLFQGP (SEQ ID NO: 3) associated with the PreScission™ cleavage tag.

In certain embodiments, the viral antigen is a viral envelope protein. In certain embodiments, the viral envelope protein is a HCV E1 or E2 protein. The HCV E2 structure, which corresponds to residues 384-746 of the viral polyprotein (E1 is residues 192-383).

In certain embodiments, the viral protein comprises the HCV E2 sequence THTVGGSAAQTTGRLT-SLFDMGPRQKIQLVNTNGSWHINRTALNCNDSLHTG-FIASLFY THSFNSSGCPERMSACRSIEAFRVGWGAL-QYEDNVTNPEDMRPYCWHYPPRQCGVVSA KTVCG-PVYCFTPSPVVVGTTDRLGAPTYTWGENETDVF-LLNSTRPPLGSWFGCTWMNS SGYTKTCGAPPCR-TRADFNASTDLLCPTDCFRKHPDTTYLKCGSGPWLT-PRCLIDYPYR LWHYPCTVNYTIFKIRMYVGGVEH-RLTAACNFTRGDRCNLEDRDRS (SEQ ID NO: 4) or variants thereof. In certain embodiments, a variant comprises one or two amino acid substitutions. In certain embodiments, a variant comprises three or four amino acid substitutions. In certain embodiments, a variant comprises four or five amino acid substitutions. In certain embodiments, the substitutions are conserved substitutions. In certain embodiments, the variant has greater than 80%, 85%, 90%, 95%, 96%, 97%, 98% or 99% sequence identity or similarity.

In certain embodiments, term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity.

In certain embodiments, sequence "identity" refers to the number of exactly matching amino acids (expressed as a percentage) in a sequence alignment between two sequences of the alignment calculated using the number of identical positions divided by the greater of the shortest sequence or the number of equivalent positions excluding overhangs wherein internal gaps are counted as an equivalent position. For example, the polypeptides GGGGGG and GGGGT have a sequence identity of 4 out of 5 or 80%. For example, the polypeptides GGGPPP and GGGAPPP have a sequence identity of 6 out of 7 or 85%. In certain embodiments, any recitation of sequence identity expressed herein may be substituted for sequence similarity. Percent "similarity" is used to quantify the similarity between two sequences of the alignment. This method is identical to determining the identity except that certain amino acids do not have to be identical to have a match. Amino acids are classified as matches if they are among a group with similar properties according to the following amino acid groups: Aromatic—F Y W; hydrophobic-A V I L; Charged positive: R K H; Charged negative—D E; Polar—S T N Q. The amino acid groups are also considered conserved substitutions.

The term "recombinant" when made in reference to a nucleic acid molecule refers to a nucleic acid molecule which is comprised of segments of nucleic acid joined together by means of molecular biological techniques. The term "recombinant" when made in reference to a protein or a polypeptide refers to a protein molecule which is expressed using a recombinant nucleic acid molecule.

The terms "vector" or "expression vector" refer to a recombinant nucleic acid containing a desired coding sequence and appropriate nucleic acid sequences necessary for the expression of the operably linked coding sequence in a particular host organism or expression system, e.g., cellular or cell-free. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

Protein "expression systems" refer to in vivo and in vitro (cell free) systems. Systems for recombinant protein expression typically utilize cells transfecting with a DNA expression vector that contains the template. The cells are cultured under conditions such that they translate the desired protein. Expressed proteins are extracted for subsequent purification. In vivo protein expression systems using prokaryotic and eukaryotic cells are well known. Also, some proteins are recovered using denaturants and protein-refolding procedures. In vitro (cell-free) protein expression systems typically use translation-compatible extracts of whole cells or compositions that contain components sufficient for transcription, translation and optionally post-translational modifications such as RNA polymerase, regulatory protein factors, transcription factors, ribosomes, tRNA cofactors, amino acids and nucleotides. In the presence of an expression vectors, these extracts and components can synthesize proteins of interest. Cell-free systems typically do not contain proteases and enable labeling of the protein with modified amino acids. Some cell free systems incorporated encoded components for translation into the expression vector. See, e.g., Shimizu et al., Cell-free translation reconstituted with purified components, 2001, Nat. Biotechnol., 19, 751-755 and Asahara & Chong, Nucleic Acids Research, 2010, 38(13): e141, both hereby incorporated by reference in their entirety.

A "selectable marker" is a nucleic acid introduced into a recombinant vector that encodes a polypeptide that confers a trait suitable for artificial selection or identification (report gene), e.g., beta-lactamase confers antibiotic resistance, which allows an organism expressing beta-lactamase to survive in the presence antibiotic in a growth medium. Another example is thymidine kinase, which makes the host sensitive to ganciclovir selection. It may be a screenable marker that allows one to distinguish between wanted and unwanted cells based on the presence or absence of an expected color. For example, the lac-z-gene produces a beta-galactosidase enzyme which confers a blue color in the presence of X-gal (5-bromo-4-chloro-3-indolyl-β-D-galactoside). If recombinant insertion inactivates the lac-z-gene, then the resulting colonies are colorless. There may be one or more selectable markers, e.g., an enzyme that can complement to the inability of an expression organism to synthesize a particular compound required for its growth (auxotrophic) and one able to convert a compound to another that is toxic for growth. URA3, an orotidine-5' phosphate decarboxylase, is necessary for uracil biosynthesis and can complement ura3 mutants that are auxotrophic for uracil. URA3 also converts 5-fluoroorotic acid into the toxic compound 5-fluorouracil. Additional contemplated selectable markers include any genes that impart antibacterial resistance or express a fluorescent protein. Examples include, but are not limited to, the following genes: amp$^r$, cam$^r$, tet$^r$, blasticidin$^r$, neo$^r$, hyg$^r$, abx$^r$, neomycin phosphotransferase type II gene (nptII), p-glucuronidase (gus), green fluorescent protein (gfp), egfp, yfp, mCherry, p-galactosidase (lacZ), lacZa, lacZAM15, chloramphenicol acetyltransferase (cat), alkaline phosphatase (phoA), bacterial luciferase (luxAB), bialaphos resistance gene (bar), phosphomannose isomerase (pmi), xylose isomerase (xylA), arabitol dehydrogenase (atlD), UDP-glucose:galactose-1-phosphate uridyltransferasel (galT), feedback-insensitive α subunit of anthranilate synthase (OASA1D), 2-deoxyglucose (2-DOGR), benzyladenine-N-3-glucuronide, E. coli threonine deaminase, glutamate 1-semialdehyde aminotransferase (GSA-AT), D-amino acidoxidase (DAAO), salt-tolerance gene (rstB), ferredoxin-like protein (pflp), trehalose-6-P synthase gene (AtTPS1), lysine racemase (lyr), dihydrodipicolinate synthase (dapA), tryptophan synthase beta 1 (AtTSB1), dehalogenase (dhlA), mannose-6-phosphate reductase gene (M6PR), hygromycin phosphotransferase (HPT), and D-serine ammonialyase (dsdA).

A "label" refers to a detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In one example, a "label receptor" refers to incorporation of a heterologous polypeptide in the receptor. A label includes the incorporation of a radiolabeled amino acid or the covalent attachment of biotinyl moieties to a polypeptide that can be detected by marked avidin (for example, streptavidin containing a fluorescent marker or enzymatic activity that can be detected by optical or colorimetric methods). Streptavidin is a protein purified from the bacterium Streptomyces avidinii. Streptavidin homo-tetramers have a high affinity for biotin. Various methods of labeling polypeptides and glycoproteins are known in the art and may be used.

Other examples of labels for polypeptides include, but are not limited to, the following: radioisotopes or radionucleotides (such as $^{35}$S or $^{131}$I) fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

In certain embodiments, the disclosure relates to recombinant polypeptides comprising sequences disclosed herein or variants or fusions thereof wherein the amino terminal end or the carbon terminal end of the amino acid sequence are optionally attached to a heterologous amino acid sequence, label, or reporter molecule.

In certain embodiments, the disclosure relates to the recombinant vectors comprising a nucleic acid encoding a polypeptide disclosed herein or fusion protein thereof.

In certain embodiments, the recombinant vector optionally comprises a mammalian, human, insect, viral, bacterial, bacterial plasmid, yeast associated origin of replication or gene such as a gene or retroviral gene or lentiviral LTR, TAR, RRE, PE, SLIP, CRS, and INS nucleotide segment or gene selected from tat, rev, nef, vif, vpr, vpu, and vpx or structural genes selected from gag, pol, and env.

In certain embodiments, the recombinant vector optionally comprises a gene vector element (nucleic acid) such as a selectable marker region, lac operon, a CMV promoter, a hybrid chicken B-actin/CMV enhancer (CAG) promoter, tac promoter, T7 RNA polymerase promoter, SP6 RNA polymerase promoter, SV40 promoter, internal ribosome entry site (IRES) sequence, cis-acting woodchuck post regulatory element (WPRE), scaffold-attachment region (SAR), inverted terminal repeats (ITR), FLAG tag coding region, c-myc tag coding region, metal affinity tag coding region, streptavidin binding peptide tag coding region, polyHis tag coding region, HA tag coding region, MBP tag coding region, GST tag coding region, polyadenylation coding region, SV40 polyadenylation signal, SV40 origin of replication, Col E1 origin of replication, f1 origin, pBR322 origin, or pUC origin, TEV protease recognition site, loxP site, Cre recombinase coding region, or a multiple cloning site such as having 5, 6, or 7 or more restriction sites within a continuous segment of less than 50 or 60 nucleotides or having 3 or 4 or more restriction sites with a continuous segment of less than 20 or 30 nucleotides.

Methods of Use

The ability of the constructs of the present disclosure to be used in methods enabling characterization of HCV- or other viral-specific B cells in acutely infected patients will provide much needed knowledge of the correlates of the humoral immune response associated with spontaneous resolutions of HCV infection. Generation of a B cell tetramer in accordance with the methods of the present disclosure enables deeper characterization of the B cell sub populations that are involved, as well as their activation level or exhaustion status.

As will be understood by the skilled artisan upon reading this disclosure, substitution of an alternative viral protein or functional fragment thereof into the construct of the present disclosure can be routinely performed in accordance with teachings herein and will result in a tetramer useful in identifying and isolating antigen specific B cells relevant to that virus and cloning antibodies thereto.

Thus, the present disclosure provides methods for use of the tetramers in identifying and isolating antigen specific B cells and cloning antibodies thereto for various viruses including, but in no way limited to, respiratory viral infections, hepatitis C virus, Zika, Dengue, human immunodeficiency virus and influenza. In these methods, a sample of a subject suspected to be infected with the virus can be contacted with the tetramer to identify and isolate antigen specific B cells in the sample. Once isolated, the antigen specific B cells can be used to clone antibodies thereto. Examples of samples which can be used in these methods include, but are not limited to, blood, plasma, PBMCs, bone marrow, liver, spleen, lung aspirates, urine, spinal fluid, or lymph obtained from a subject suspected of being infected with the virus.

To identify antigen specific B cells in a sample, the sample is contacted with the tetramer under conditions in which the tetramer binds to any antigen specific B cells in the sample. Bound tetramer indicative of antigen specific B cells in the sample is then detected. In one non-limiting embodiment, the tetramer is labeled with a fluorophore that can be detected by a FACsort machine with appropriate lasers.

To isolate antigen specific B cells from a sample, the sample is again contacted with the tetramer under conditions in which the tetramer binds to any antigen specific B cells in the sample. Any bound cells are can be isolated using, for example, a FACsort machine.

Tetramers of the present disclosure can also be used to clone antibodies specific to the antigen specific B cells. In one non-limiting embodiment, once bound to the tetramer, single antigen specific B cells are sorted by a FACsort machine. Cells are then lysed and their RNA is reverse transcribed. Heavy and light chains are then amplified using PCR and nucleotide specific primers. These PCR fragments can then be sequenced to allow for differentiation between different subtypes of antibodies, e.g. IgG1, IgG2, IgM etc. These can then be cloned into expression vectors and expressed as monoclonal antibodies.

The following section provides further illustration of the compositions and methods of the present disclosure. These working examples are illustrative only and are not intended to limit the scope of the disclosure in any way.

E2 Glycoprotein Tetramer Detects Hepatitis C Virus-Specific Memory B Cells

Investigation of the humoral responses during acute HCV infection have been limited by the inability to directly identify and characterize HCV-specific B cells. Disclosed herein is a tetramer of the E2 glycoprotein ectodomain (J6, genotype 2a strain), which allows one to visualize E2-specific B cells longitudinally in the peripheral blood of HCV-infected individuals. HCV-specific class-switched memory B cells were detected in 3 out of 7 participants during late acute infection, with a mean frequency of 0.63% for positive samples (range 0.16-0.67%) and in 7 out of 7 participants with chronic infection with a mean frequency of 0.47% (range 0.20-0.78%). In a cross-sectional study, E2 tetramer positive population was detected in 28 out of 31 chronically infected individuals. Deep sequencing of the BCR from E2-specific class-switched memory B cells sorted from two independent participants revealed a focused repertoire suggestive of clonal selection. Tetramer-specific B cells exhibited skewed CDR3 length distribution and increased mutation frequency compared with naive B cells. This BCR profile is indicative of clonal expansion and affinity maturation. E2 tetramer allows for specific and sensitive ex vivo characterization of rare HCV-specific B cells in infected individuals.

Disclosed herein is an HCV-specific B cell tetramer reagent composed of the ectodomain of HCV envelope glycoprotein E2 (J6 strain, genotype 2a). The specificity of this tetramer was validated using an E2-specific hybridoma cell line and PBMCs from subjects persistently infected with HCV of different genotypes. To better understand the kinetics of Ag-specific B cell responses during HCV infection, a longitudinal study was performed to directly visualize and quantify the frequency of E2-specific B cells in the peripheral blood of subjects progressing from an acute to chronic infection. The HCV E2 tetramer enables one to isolate E2-specific class-switched memory B cells and perform BCR deep sequencing on two persistently HCV-infected subjects. The dominant repertoire profiles, skewed CDR3 length distributions, and increased mutation frequencies all suggested that these cells were selected, expanded, and had undergone affinity maturation processes.

In humans, a study from a cohort of a single-source outbreak of HCV infection showed that the rapid development of neutralizing Abs correlated with spontaneous clearance. However, other reports described cases where HCV infection was spontaneously resolved without the detection of HCV-specific Abs in humans. The development of methods enabling characterization of HCV-specific B cells in acutely infected patients is needed to establish better understanding of the correlates of the humoral immune response associated with spontaneous resolutions of HCV infection. Generation of B cell tetramer is an significant improvement because it enables deeper characterization of the B cell subpopulation that is involved, as well as its activation level or exhaustion status. Previously, a gp41 B cell tetramer was successfully used to study the development of the Ab responses in the context of HIV infection. The ectodomain of HCV glycoprotein E2 from a genotype 2a strain (J6) was used to develop a biotinylated monomer that could be used to generate a tetramer specifically recognizing HCV E2-specific B cells and validated using E2-specific Abs and hybridoma cells producing E2-specific Abs.

Figure 3A:
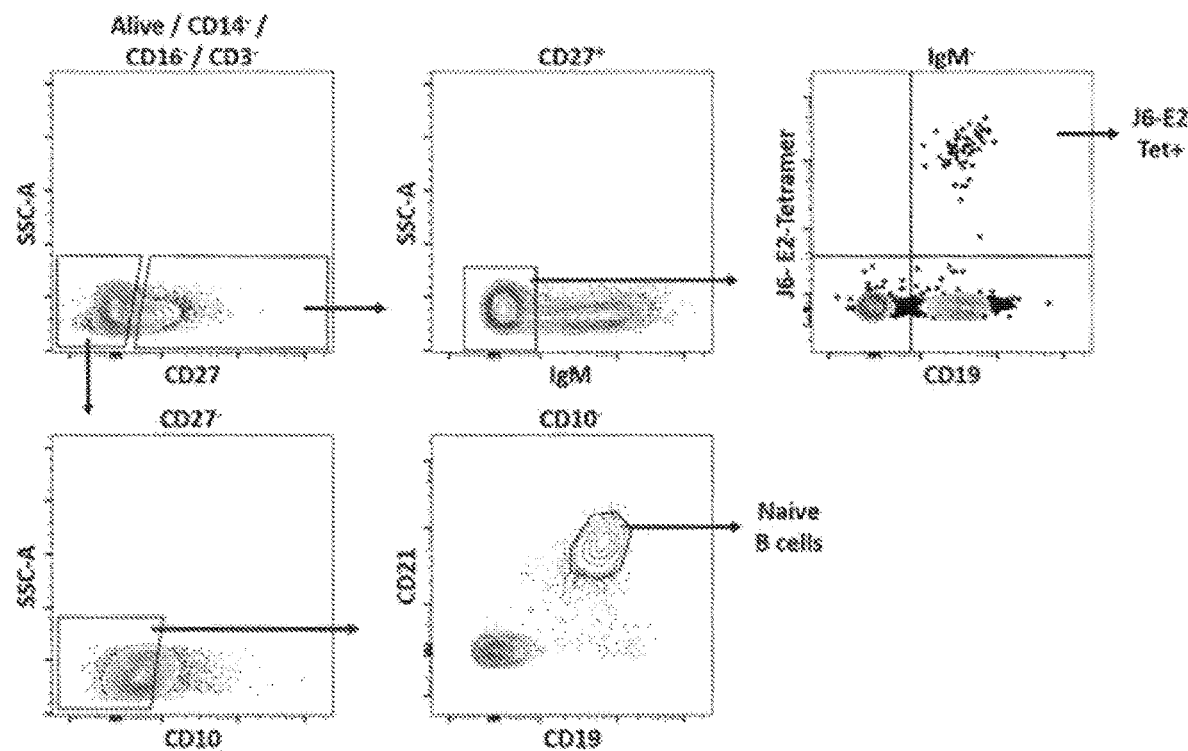
FIG. 3A shows data indicating the identification of HCV E2-specific class-switched memory B cells in the peripheral blood of chronic HCV participants using J6-E2 tetramer. Gating strategy. Cells were first gated on live single CD142, CD162, CD32 lymphocytes (not shown). Naive B cells were defined as CD272, CD102, CD19+ and CD21hi. Class-switched memory B cells were defined as CD27+, IgM2 and CD19+. HCV E2-specific cells were identified using J6-E2 tetramer. Positive tetramer gate was set relative to background staining observed on CD192 B cells.
Figure 3B:
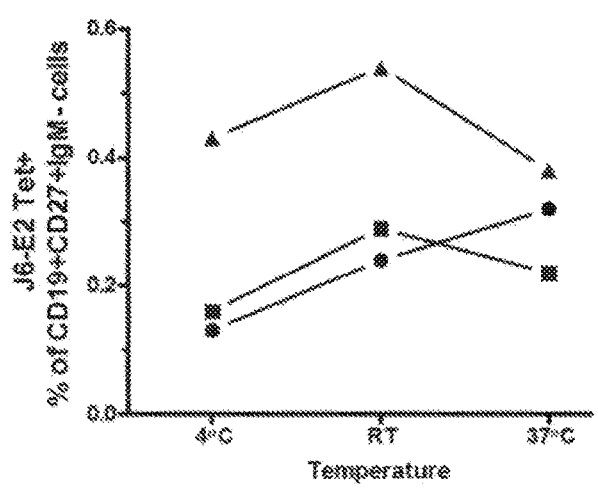
FIG. 3B shows tetramer staining performed at three different temperatures for three independent samples. Room temperature staining was selected and used throughout the study.
Figure 3C:
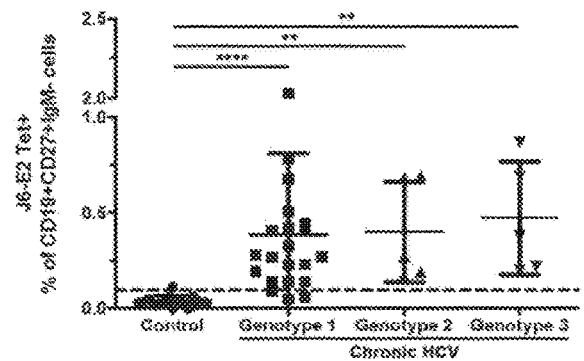
FIG. 3C shows cumulative flow cytometry data for ex vivo staining of PBMCs using J6-E2 tetramer and B cell markers in uninfected controls (healthy donors and naive PWID combined; n=13) and chronic HCV participants (n=31). Each dot represents the percentage of tetramer positive cells within class-switched memory B cells (CD19+ CD27+IgM2) from one subject. Lines represent the mean in all groups and error bar represents the SD. Threshold (dotted line) of detection was set at 0.095% (mean detection from uninfected controls+2 SD).
Figure 3D:
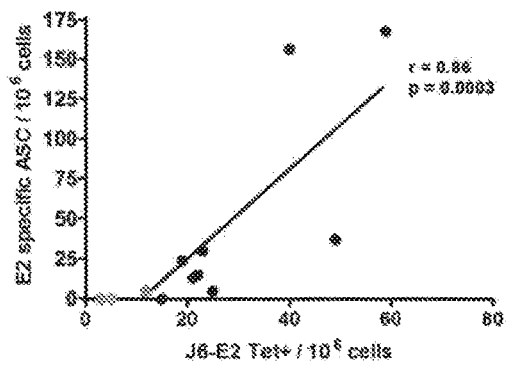
FIG. 3D shows data indicating a correlation between tetramer staining and IgG B cell ELISPOT (n=12). Tetramer positive cells were expressed as number of positive cell/1 3 106 PBMCs. E2-specific IgG ELISPOT data were expressed as the number of E2-specific ASC/1 3 106 PBMCs. Spearman r and p values are indicated.

Ag-specific B cells were identified in HCV-infected subjects using the E2 tetramer. The most frequent genotype in the Montreal Acute Hep C Cohort Study is genotype 1. Despite high variability of sequences between genotypes (identity<70%), especially in the hypervariable regions of E2 (HVR1-3), exposed conserved regions are present and have been shown to be important for the binding of E2 protein with the co-receptor CD81 protein on the cell surface and subsequent viral entry. Cross-reactive human Abs have been described that bind various E2 proteins from multiple HCV genotypes. Two different E2 tetramers were tested that were derived from genotype 1 (H77 strain) and genotype 2 (J6 strain) with PBMC samples obtained from genotype 1, 2, and 3 infected participants. The staining of Ag-specific B cell with the J6-E2 tetramer was far more specific as compared with the H77-E2 tetramer. The H77-E2 tetramer staining had increased background levels and there was less intensity in signal. As a result, all experiments were done using the J6-E2 tetramer. With this tetramer, E2-specific class-switched memory B cells were detected in the majority of chronically infected individuals (18 out of 21 for genotype 1 and 5 out of 5 for both genotypes 2 and genotype 3, FIG. 3C). Therefore, the usage of a different E2 genotype (J6, 2a) did not affect binding of Ag-specific B cells from patients with different infection genotypes. Furthermore, the sensitivity of the tetramer was comparable to the B cell ELISPOT assay as shown in FIG. 3D.

Figure 4A:
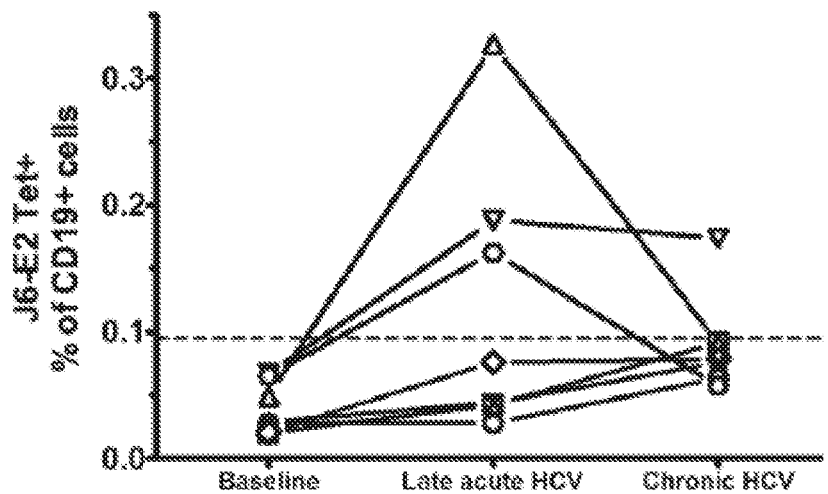
FIG. 4A shows data on a longitudinal analysis of HCV E2-specific B cells during acute HCV infection progressing to chronicity. J6-E2 tetramer positive B cells were detected longitudinally in individuals that developed a chronic HCV infection (n=7). Three key time points were tested: Baseline (0.1.5 mo prior to EDI); Late acute HCV (5 6 2 mo post EDI); and Chronic HCV (0.12 mo post EDI). Each dot represents the percentage of tetramer positive cells from one subject in total CD19+ B cells
Figure 4B:
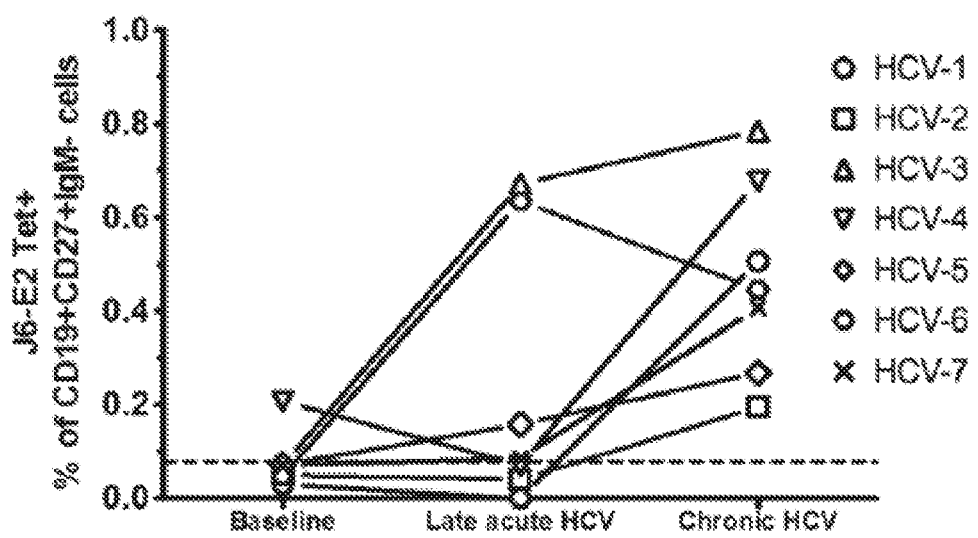
FIG. 4B shows data in class-switched memory B cells (CD19+CD27+IgM2). Dotted line represents the threshold for tetramer positive signal.

In a longitudinal analysis, tetramer positive populations could only be detected in approximately half of the tested individuals during the late acute HCV infection (FIG. 4A, 4B). This was in agreement with the anti-E2 titer, measured by ELISA where only the samples with a positive tetramer population exhibited a detectable anti-E2 titer (FIG. 4C). This is consistent with previous reports showing a delayed Ab response during acute infection. It suggests that at least in some patients, the development and/or expansion of HCV E2-specific B cells is hindered, which may be a factor that contributes to the establishment of a chronic infection. It is also possible that early HCV-specific B cells are of lower affinity and thus are unable to bind the E2 tetramer efficiently. To expand this analysis, in a preliminary experiment, HCV-specific B cells were detected in three out of six subjects after spontaneous resolution of HCV infection with a mean frequency of 0.3% (range: 0.15-0.49%) of class-switched memory B cells (1 y post EDI, data not shown). This is also consistent with a previous report that showed Ab responses during HCV infection are usually of low titer, and decline rapidly after spontaneous resolution. Analysis of the E2 tetramer positive population frequency and function longitudinally during earlier time points in a larger cohort of participants with different infection outcomes may provide more detailed insight into the role of these Ag-specific B cells in determining the course and outcome of HCV infection.

The tetramer construct will allow one to characterize the phenotype of HCV-specific B cells in greater detail. In the genotype 1 chronically infected subjects, one cal also detect HCV-specific unswitched memory B cells (CD27+IgM+), and to a lower extent naive/atypical B cells (CD27−IgM+), but the frequency of HCV-specific class-switched memory B cells was certainly higher in the majority of samples analyzed (15 out of 21, FIG. 3E).

HCV E2-specific class-switched memory B cells were sorted using the E2 tetramer for BCR deep sequencing. In two independent subjects, the HCV-specific BCR repertoire was focused, suggestive of Ag driven selection. Moreover, the normal Gaussian-like distribution of CDR3 lengths was skewed in both participants analyzed, suggesting an amplification and/or selection of specific clonotypes. It is also postulated that the affinity maturation leads to a shorter CDR3 length in Ag-specific B cells. However, differences were not observe between the average CDR3 length of naive B cells and HCV E2-specific cells in the two subjects analyzed. Also, the accumulation of mutations in the CDR3 sequence is indicative of affinity maturation process. Analysis indicated an increased mutation frequency in HCV-specific BCRs compared with naive receptors. Together these results suggest that sorted E2-specific class-switched memory B cells were indeed Ag-specific, selected, expanded, and accumulated mutations during the affinity maturation process.

The BCR repertoire of bulk memory and naive B cells was previously investigated during HCV infection. However, in this study total memory B cells as opposed to Ag-specific cells were analyzed. It was shown that the gene usage was distinct between those who spontaneously resolved the infection versus those who were chronically infected. Also, the clonality of the repertoire was greater in resolving infection compared with chronically infected individuals. Phylogenetic analysis demonstrated tight clustering of a limited number of related B cell clonotypes in resolvers compared with a more dispersed pattern in chronically infected individuals, suggestive of an increased clonal selection in the resolvers. Finally, in the same report, the CDR3 length distribution was particularly skewed in BCRs of subjects who resolved the infection with a single CDR3 length being the dominant clone compared with BCRs obtained from persistent infection where the deviation from the Gaussian-like distribution was less apparent. Utilizing HCV E2-specific tetramers will now enable us to investigate the evolution of the repertoire in HCV-specific B cells, in particular the association of distinct BCR gene family usage among individuals who spontaneously clear versus those that progress to chronicity. One limitation of this approach is the low frequency of HCV-specific B cells. Nevertheless, given the advent of sensitive technologies, we are hopeful that the longitudinal comparisons of the BCR repertoire at the single cell level from subjects with different infection outcomes will be feasible in the near future, as this important tool will allow for a better characterization of HCV-specific B cells.

B cell disorders such as mixed cryoglobulinemia and non-Hodgkin lymphomas are complications associated with chronic HCV infection. Clonal B cell expansion in the liver is associated with these extrahepatic manifestations. Furthermore, E2-specific B cells isolated from an asymptomatic HCV patient used the VH01-69 gene that is associated with B cell lymphomas in chronic HCV. B cells were also implicated in liver fibrosis, where they have been shown to be activated, produce inflammatory cytokines, and constitutively secrete IgG. Isolation and characterization of HCV-specific B cells in individuals with such phenotypes will provide a better insight into the role of B cells in these aberrant manifestations and may provide better B cell-based immunotherapies. Little is known about the interaction between B cells and CD4 helper T cells, specifically the follicular helper T cells (Tfh) during an acute and chronic HCV infection. HCV-specific Tfh cells had an activated phenotype during the acute phase of HCV infection, with an increased expression of ICOS, which correlated with Ab production. Studies combining HCV-specific B cell visualization (together with subset identification, activation, and exhaustion markers) with detailed analyses of the neutralizing Ab repertoire and Tfh development and function could elucidate the importance of this interaction and how it influences the generation of virus-specific neutralizing Abs and infection outcome prognoses.

Expression and Purification of Niotinylated E2 Ectodomain

The pCMJJ4 vector served as the backbone for expression of the HCV E2 ectodomain (J6 genotype 2a strain, aa 384-664). The E2 ectodomain sequence was linked to a BirA substrate peptide (GLNDIFEAQKIEWHE) (BSP85) (SEQ ID NO: 2), followed by a PreScission protease-cleavable protein A (PA) tag (FIG. 1A). Lentiviruses were generated as described in Naldini et al. 1996. In vivo gene delivery and stable transduction of nondividing cells by a lentiviral vector. Science 272: 263-267. The E2 expression vector and accessory plasmids (psPAX2 and pMD2G) were introduced into HEK293T cells by calcium phosphate transfection. Supernatants containing lentiviruses were harvested 3 days later and were subsequently used to transduce HEK293T cells expressing the BirA enzyme, which biotinylates the BirA substrate peptide. Analysis of surface Thy1.1 expression was used to determine transduction efficiency. Cells expressing Thy1.1 were then inoculated into CELLine Flasks (Integra Biosciences, Hudson, N.H.) and supernatants were harvested every 7 d. The supernatants were clarified by centrifugation at 5000×g for 30 min at 4° C. and E2-biotin-protein A was purified by the use of an IgG fast flow affinity column (GE Healthcare, Atlanta, Ga.). The protein A tag was removed by cleavage with 50:1 ratio of protein to PreScission protease (GE Healthcare) overnight at 4° C. E2-biotin was subsequently purified with an IgG FF column (GE Healthcare) to remove uncleaved E2-protein A and the protein A tag. Finally, a GSTrap FF column was used to remove PreScission™ protease (GE Healthcare). As a control reagent, an HIV gp140 tetramer (clade C HIV-1, isolate DU422) was also generated using the same approach.

Study Participants

Study subjects were recruited among people who inject drugs (PWID) participating in the Montreal Acute Hep C Cohort Study (HEPCO) or presenting to the hepatology clinic of St-Luc Hospital. Acute infection was identified and followed. The estimated date of infection (EDI) was defined as the median point between the last negative and the first positive HCV test. Chronic HCV infection was defined as a positive HCV RNA test at 6 mo following the EDI. A total of 37 subjects were examined in a cross-sectional analysis: 31 chronic patients (HCV Ab+ve and HCV RNA+ve) and 6 spontaneous resolvers (HCV Ab+ve and HCV RNA−ve). In addition, seven PWIDs were analyzed longitudinally at three key time points before, during, and after acute HCV infection: baseline (negative both for HCV RNA and Abs), late acute phase (5±2 mo post EDI) and chronic phase (>12 mo post EDI). Two control groups consisting of seven healthy donors and six HCV naive PWID were also included. Participant's demographics and clinical characteristics are listed in Table I. Experiments were performed on cryopreserved PBMCs.

and stained with the tetramer for 30 min at room temperature. Cells were washed twice with FACS buffer and stained with either panel 1 (FIGS. 3, 4) or panel 2 (cell sorting) for 30 min at 4° C. Cells were washed again twice and fixed with 1% formaldehyde in PBS before FACS analysis. The following conjugated anti-human mAbs were used in panel 1: CD3-Pacific Blue (clone UCHT1), CD14-V500 (clone M5E2), CD16-V500 (clone 3G8), CD19-Alexa Fluor 700 (clone HIB19), CD27-allophycocyanin-H7 (clone M-T271), IgM-BB515 (clone G20-127). Panel 2 contained all panel 1 Abs with the addition of CD10-BV605 (clone HI10a) and CD21-PE-Cy7 (clone B-ly4). All Abs were obtained from BD Biosciences. Live cells were identified using LIVE/DEAD fixable aqua dead cell stain kit (Molecular Probes; Thermo Fisher Scientific). Multiparameter flow cytometry was performed at the flow cytometry core of the CRCHUM using a BD LSRII instrument and cell sorting was completed using a BD Aria IIIu instrument, both equipped with violet (405 nm), blue (488 nm), yellow-green (561 nm) and red (633 nm) lasers and FACSDiva version 8.0.1 (BD Biosciences). FCS data files were analyzed using FlowJo version 10.0.8 for Mac (Tree Star, Ashland, Oreg.). Fluorescence minus one controls were used to set the gate for CD27 and CD10. B cell gating included the selection of live cells that are also CD14—, CD16− and CD3− (FIG. 3A).

E2 ELISA

HCV E2 glycoprotein (30) (1 µg/ml in 0.1 M Na2CO3 buffer) was used to coat 96-well flat bottom immuno plates (Nalgene Nunc; Thermo Fisher Scientific) overnight at 4° C. Coated plates were washed twice with PBS plus 0.05% Tween 20 (PBS-T) and then blocked with 10% normal goat serum in PBS-T (Jackson ImmunoResearch, West Grove, Pa.) for 1 h at 37° C. Human plasma samples from HCV-1 to HCV-7 as well as three healthy controls were added to the plates (10-fold serial dilutions in binding buffer [0.1% normal goat serum in PBS-T]) for 90 min at room temperature and the plates were washed eight times with PBS-T. Then, 0.1 µg/ml biotinylated anti-human IgG mAb MT178/145 (Mabtech, Cincinnati, Ohio) diluted in binding buffer was added to each well for 90 min at room temperature and plates were washed eight times with PBS-T. Streptavidin-

TABLE 1

Demographics and clinical characteristics of study subjects

| | Acute to Chronic HCV (n = 7) | Chronic HCV (n = 24) | Resolvers (n = 6) | Naive PWID (n = 6) | Healthy Donors (n = 7) |
|---|---|---|---|---|---|
| Sex (M/F) | 7/0 | 18/6 | 4/2 | 5/1 | 4/3 |
| Median age (y) | 29 | 43 | 26 | 27 | 32 |
| HCV genotype (1a/1b/2/3/3a/ND) | 1/6/−/−/−/− | 10/2/5/1/4/2 | 4/2/−/−/−/− | NA | NA |
| Median time point tested (y postinfection) | NA | 4 | NA | NA | NA |
| Median time point tested (d post EDI) | Baseline: −46 Late acute: 155 Chronic HCV: 554 | NA | 427 | NA | NA |

Human PBMC Staining and Flow Cytometry

PBMCs from healthy controls and HCV-infected individuals were thawed and blocked with RPMI 1640 supplemented with 20% heat-inactivated human serum and 5 µl human Fc block/2×10⁶ cells (BD Biosciences, Mississauga, ON) for 15 min at 4° C. Cells were then washed with FACS buffer (PBS 1×[Wisent], 1% FBS [FBS; Sigma], 0.01% sodium azide [Thermo Fisher Scientific, Burlington, ON])

HRP (Mabtech) diluted 1:5000 in binding buffer was added to plates for 45 min at room temperature and plates were washed eight times with PBS-T. Tetramethylbenzidine substrate (BD, Franklin Lakes, N.J.) was added to develop color according to the manufacturer. Absorbance (450 nm) was measured using a Versamax microplate reader and SoftMax-Pro software (Molecular Devices, Sunnyvale, Calif.). Standard curves were done using serial dilutions of E2 mAb 2C1, goat anti-mouse IgG, biotin conjugate (Invitrogen, Thermo Fisher Scientific, Waltham, Mass.). The assay was quantified Elisaanalysis.com software.

Human IgG ELISPOT

B cell ELISPOT was performed with the human IgG ELISPOT kit (Mabtech) according to the manufacturer's instructions. Briefly, PBMCs were thawed and rested for 1 h at 37° C., 5% CO2 in R10 (RPMI 1640, supplemented with 10% FBS). Cell were stimulated with 1 µg/ml R848 and 10 ng/ml rhIL-2 in AIM-V supplemented with 10% FBS (AIM-V-FBS) in a 24 wells plate at 2×10⁶ cells/well or left unstimulated for 72 h at 37° C., 5% CO2. Cells were washed three times and plated in duplicates in PVDF MSIPS4W10 ELISPOT plates (EMD Millipore, Etobicoke, ON) that were previously coated with anti-IgG (MT91/145; Mabtech) overnight at 4° C., washed and blocked with AIM-V-FBS for 1 h at 37° C., 5% CO2. Plates were incubated 18 h at 37° C., 5% $CO_2$. Plates were washed nine times with PBS-T. Total IgG response was detected with anti-IgG-biotin (MT78/145) and HCV-specific Ab response was detected with J6-E2-biotin, for 2 h at room temperature. Plates were washed nine times and incubated with streptavidin-ALP (alkaline phosphatase, 1:1000; Mabtech) for 1 h at room temperature. Plates were washed seven times with PBS-T, three times with PBS, and one time with water. Spots were developed with the alkaline phosphatase conjugate substrate kit (Bio-Rad, Montreal, QC) for 4 min in the dark, according to the manufacturer's instructions. Plates were extensively washed with tap water, dried overnight and spots were counted with Immunospot plate reader (Cellular Technology, Shaker Heights, Ohio) and normalized to Ab-secreting cells (ASC)/ 1×10⁶ PBMC.

Purification and Sorting of Tetramer Positive Class-Switched Memory B Cells and Naive B Cells PBMCs were thawed and total B cells were purified by negative selection using the MACS Pan B cell Isolation Kit (Miltenyi Biotec, Auburn, Calif.) according to the manufacturer's protocol. Tetramer staining and cell surface staining for CD3, CD10, CD14, CD16, CD19, CD21, CD27, and IgM were performed as described above. Tetramer positive class-switched memory B cells (CD19+CD27+IgM−) and naive B cells (CD19+CD27−CD10−CD21hi) were FACS sorted with an Aria Mu flow cytometer (BD Biosciences).

BCR Sequencing

Sorted cells were frozen and shipped to Adaptive Biotechnologies (Seattle, Wash.) for genomic DNA extraction and BCR H chain (IGH) deep sequencing. Lists of unique CDR3 sequences (clonotypes) and their frequency within the repertoire were obtained for each sample. Data were filtered to remove out-of-frame sequences and sequences with stop codons within the CDR3 region. Clonotypes with sequence counts equivalent to or less than the average count per cell were also removed from the analysis. Data were analyzed using the ImmunoSEQ analysis platform. To study the dominance profile, clonotypes were classified into four groups according to their frequency within the repertoire. The first group was composed of dominant clonotypes that were each present at a frequency>1% of the repertoire. The second group comprised subdominant clonotypes, with frequencies between 0.1 and 1% of the repertoire. The third group was made of low abundance clonotypes with frequencies between 0.05 and 0.1% of the repertoire. Finally, the fourth group contained clonotypes of lowest abundance with frequencies of <0.05% of the repertoire. The CDR3 region length in amino acids (aa) was determined and the distribution of the frequency of each length was analyzed. Very short (<7 aa) and very long (>31 aa) CDR3 lengths were rare and omitted from the analysis. V gene mutation frequency of each clonotype sequence was calculated as a percentage and represents the number of substitutions/100 bp compared with germline sequence according to the ImMunoGeneTics (IMGT) database.

Generation of HCV E2-Specific B Cell Tetramers

Figure 1B:
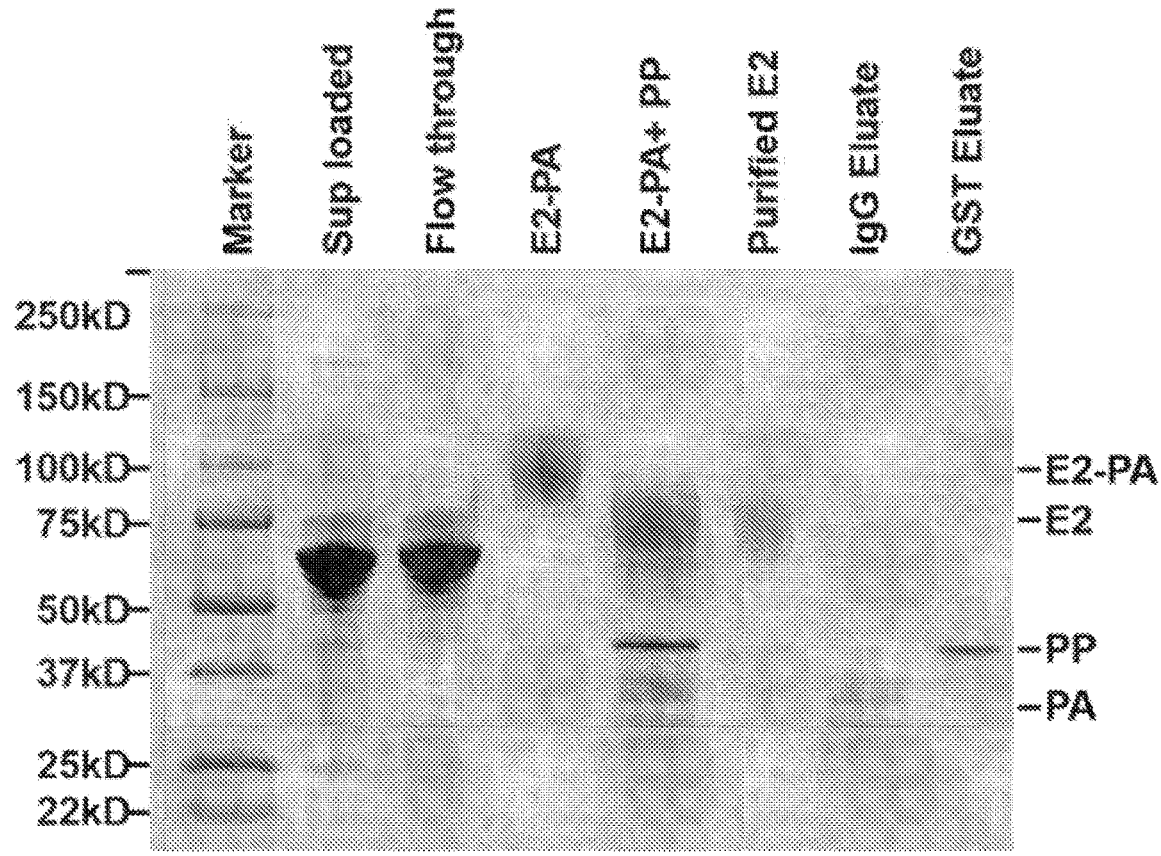
FIG. 1B shows SDS-PAGE and Coomassie Blue staining showing E2 monomer purification steps as follows: supernatants from HEK-293T cell lines expressing E2-biotin-protein A were clarified by centrifugation (Sup loaded, lane 2) and applied to the resin. The column was extensively washed to remove unbound material (Flow through, lane 3). E2-biotin-protein A was eluted off the column (E2-PA, lane 4) and incubated with PreScission protease (PP, lane 5). E2-biotin (lane 6) was further purified by removing uncleaved E2-biotinprotein A and protein A tag by IgG column and PreScission protease using GST column. The eluates from the IgG (lane 7) and GST columns (lane 8) are also shown.

In order to directly examine HCV-specific B cells, the ectodomain of HCV envelope glycoprotein E2 (aa 384-664) derived from genotype 2a (J6 strain) was used to develop a B cell tetramer capable of identifying HCV-specific B cells from the peripheral blood of infected individuals. The J6 genotype 2a strain was chosen because its ectodomain was previously successfully expressed and crystalized to resolve the E2 protein structure diffracted to 2.4 Å resolution. This protein was also shown to be properly folded when expressed in HEK293T cells. A diagram for the generation of the E2 expression vector is shown in FIG. 1A. The insertion of the biotinylation site BSP85 sequence enabled site-specific monobiotinylation, whereas the addition of a protein A tag allowed for affinity purification. Biotinylated E2 monomers were produced in lentivirus-transduced HEK293T cells. Monomer purity and size were confirmed by SDS-PAGE (FIG. 1B). Purified E2-PA (90 kDa; lane 4), was cleaved by PreScission protease (PP, 46 kDa) to remove the protein A tag (PA, 30 kDa; lane 5), and E2 monomer (expected size 60 kDa) was purified by passage over IgG then GST columns (lanes 6-8). Since the purified E2 monomers corresponded to the expected size, they were used to generate tetramers by incubation with fluorophore-conjugated streptavidin or ExtrAvidin at a molar ratio of 4:1.

Validation of E2 Tetramers Using E2-Specific Hybridoma

Figure 2A:
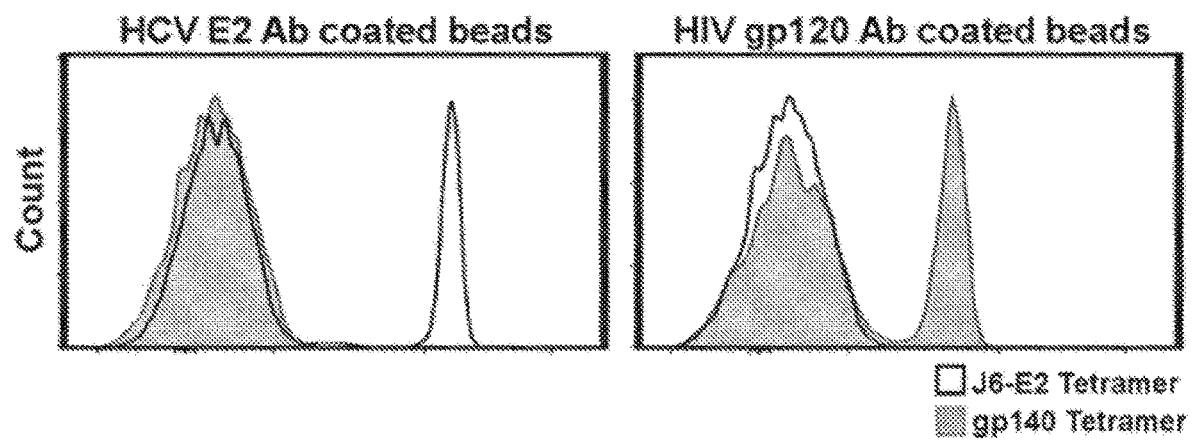
FIG. 2A shows data indication the specificity of J6-E2 tetramers. Representative flow cytometry histogram of CompBeads coated with either the E2-specific mAb 2C1 or the HIV gp120-specific mAb ID6 stained with J6-E2 (black line) or gp140 (gray shaded) tetramers. Allophycocyanin fluorescence intensity was measured and is represented as relative count for each sample
Figure 2B:
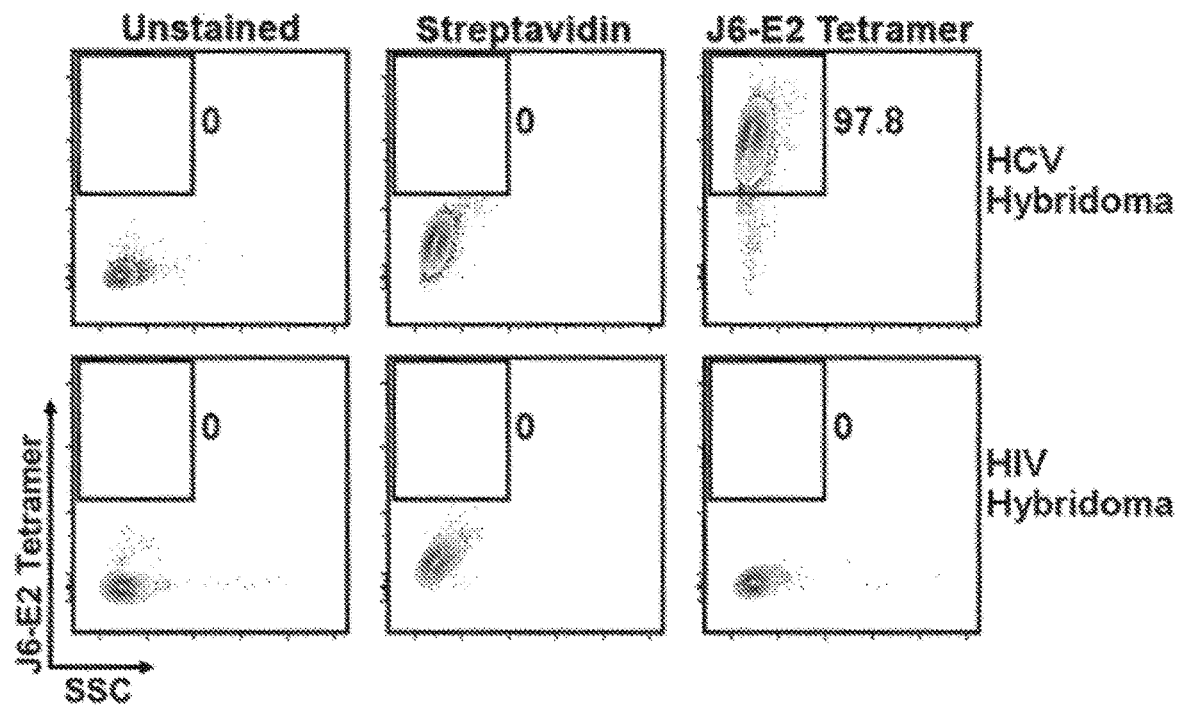
FIG. 2B shows representative flow cytometry plot of the hybridoma cell lines 2C1 (HCV E2-specific) and 1G12 (HIV gp140-specific) stained with J6-E2 tetramers. Unstained hybridomas (left panels) and hybridomas stained with allophycocyanin conjugated streptavidin (middle panels) were used as controls. Numbers denote frequencies of live tetramer-positive cells.

To confirm that the E2 tetramer reagent could specifically recognize Abs targeting the E2 glycoprotein ectodomain, E2 tetramer reactivity was validated by two approaches. First, anti-mouse Ig BD flow cytometry compensation beads (CompBeads) were incubated with either 2C1 mAb that recognizes HCV E2 glycoprotein or 1D6 mAb that recognizes HIV gp120. Next, the Ab-coated beads were incubated with E2 or gp140 tetramers, and the tetramer allophycocyanin fluorescence intensity was analyzed by flow cytometry. The E2 tetramer was able to recognize the CompBeads that were coated with the E2-specific mAb 2C1 (FIG. 2A, left). This interaction was specific, as the E2 tetramer could not recognize the HIV Ab 1D6 and the HIV-specific gp140 tetramer did not recognize the beads coated with the anti-E2 2C1 Ab. The gp140 tetramer did, however, recognize the beads containing the gp120-specific Ab 1D6 (FIG. 2A, right). Whether the HCV-E2 tetramer could directly recognize hybridoma cells that produce anti-HCV E2 mAbs was examined. The E2 tetramer was used in an intracellular staining of the hybridoma cell line (2C1) that produces a mAb to J6-E2 protein (FIG. 2B, top). The E2 tetramer stained the 2C1 hybridoma, but did not recognize the hybridoma that produces the HIV envelope protein gp140-specific Ab (1G12) (FIG. 2B, bottom). Together these data suggest that the E2 tetramer could specifically recognize Abs targeting the HCV E2 glycoprotein.

Identification of HCV E2-Specific B Cells in Chronic HCV Subjects

The capacity of the E2 tetramer to detect HCV-specific B cells in HCV-infected individuals (Table I) was evaluated. Tetramer and surface staining were performed on PBMC to identify HCV E2-specific class-switched memory B cells (CD19+CD27+IgM−) in subjects with established chronic HCV infection (HCV RNA+ve for >1 y, genotypes 1, 2, or 3; n=21, 5 and 5 respectively). A representative gating strategy is presented in FIG. 3A. The tetramer positive gate was set relative to the background staining observed on CD19− cells. Tetramer staining was evaluated at three temperatures: 4° C., room temperature, and 37° C. The staining was most efficient at room temperature, enabling detection of more HCV-specific B cells (FIG. 3B), with minimal background on control samples as compared with 37° C. Within the total class-switched memory B cell compartment, the average frequency of HCV-specific B cells was 0.40% (range 0.05-2.03%) (FIG. 3C). The mean background binding from healthy donors (n=7) and HCV negative PWID (n=6) was 0.04%, which when combined ranged from 0 to 0.11%. The threshold of detection was set at 0.095% (mean frequency+2 SD of healthy donors and naive PWID) and HCV E2-specific tetramer-positive populations were detected in 28 out of 31 chronic HCV participants.

Sensitivity of the tetramer detection was compared with the detection of HCV-specific B cells using an IgG ELISPOT assay. As shown in FIG. 3D, there was a significant correlation between the number of E2-specific ASC and the number of tetramer positive cells (Spearman r=0.86; p=0.0003). In addition, the ELISPOT assay showed that in the three samples for which we could not detect a tetramer positive population, E2-specific ASC were not detected or were barely detectable (gray dots, FIG. 3D).

Figure 3E:
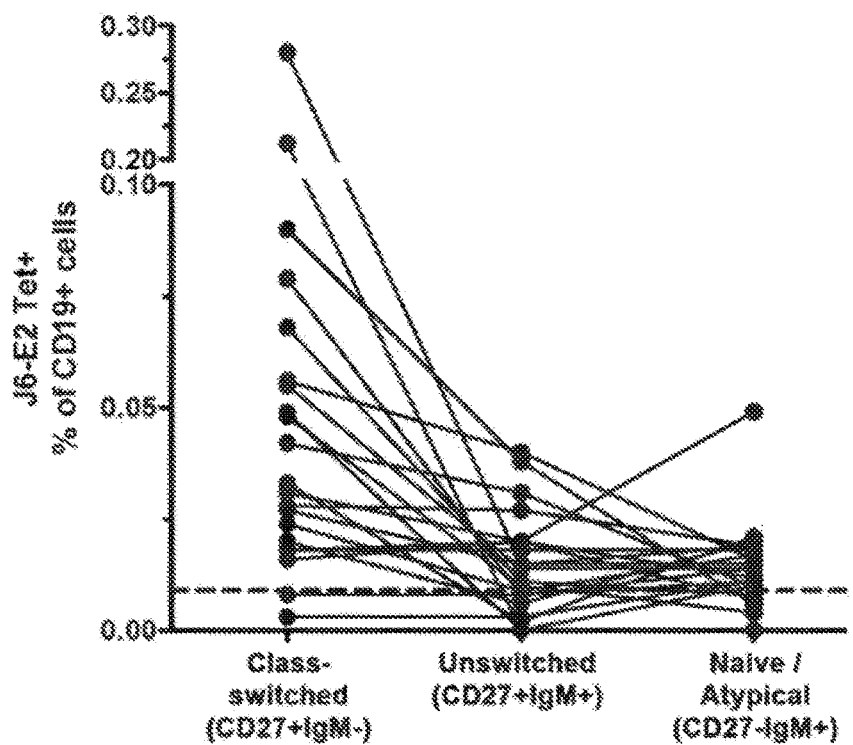
FIG. 3E shows data on cumulative flow cytometry data for genotype 1 samples (n=21) of tetramer positive populations in different B cell subsets. Class-switched memory B cells were identified as CD19+CD27+IgM2, unswitched memory B cells were identified as CD19+ CD27+ IgM+, and naive/atypical B cells were identified as CD19+ CD272IgM+.

Analyses of other B cell subsets, unswitched memory B cells (CD27+IgM+), and naive/atypical B cells (CD27−IgM+) in genotype 1 samples showed that the tetramer positive cells were detectable in both populations (FIG. 3E). However, in the majority of cases (15 out of 21, p<0.01) we detected more HCV-specific cells in the class-switched memory B cell subset. The remaining six samples had an equivalent frequency of tetramer positive cells in the unswitched memory population. There were also five samples where the frequency of naive/atypical B cells was equivalent or higher than the frequency of class-switched memory B cells, but the overall frequency of tetramer positive B cells was quite low and did not allow for a more detailed comparison of these two subsets. None of the three samples that were below the threshold of detection in class-switched memory B cells had a significant tetramer positive population in the unswitched or naive/atypical memory B cells. Collectively, these results suggest that the J6-E2 tetramer can be used to successfully identify HCV-specific B cells in infected participants and that HCV E2-specific B cells are present in the majority of individuals with chronic infection.

Detection of HCV E2-Specific B Cells During Acute HCV Infection

Identification of HCV-specific B cells during acute HCV infection would enable the characterization of early changes in that population leading to the development of the Ab response. The longitudinal frequency of HCV E2-specific B cells in acutely infected participants who went on to develop persistent HCV infection was examined (n=7). During the late acute phase of infection (5±2 mo, EDI), E2 tetramer positive cells were detected in approximately half of the samples (3 out of 7) within both the total CD19+ B cell population (FIG. 4A) and the class-switched memory B cell population (CD19+CD27+IgM−) (FIG. 4B). All participants tested (7 out of 7) developed a tetramer positive population within the class-switched memory B cell population at their latest follow-up chronic time point (>12 mo). These results suggest that at least in some participants the development of the HCV-specific B cell response was significantly delayed. ELISA assay was performed with the plasma samples from the same participants during both the late acute and chronic time points. At the late acute time point, E2-specific Abs were detected only in the three samples with a tetramer positive population (FIG. 4C). All samples showed seroconversion at the chronic time point (FIG. 4D). For the majority of the samples, there was an observable correlation between the E2 Ab titers and the frequency of tetramer positive class-switched memory B cells (FIG. 4E). The only exception was sample HCV-4 where we detected a high frequency of tetramer positive cells but very low anti-E2 Ab titers (gray dot in FIG. 4E).

The BCR Repertoire of HCV E2-Specific Class-Switched Memory B Cells is Focused

The BCR of naive and HCV-specific B cells of two subjects were sequenced to analyze the characteristics of B cell antigenic selection and maturation process within the repertoire. The selection and amplification of B cell clonotypes led to a focusing of the BCR repertoire with fewer clones detected and a dominant profile emerging. J6-E2 tetramer positive class-switched memory B cells (CD19+CD27+IgM−) from subjects HCV-8 and HCV-9 were sorted at their latest follow-up time point (≥5 y) and deep sequenced for the BCR IgH (IGH). Naive B cells (CD19+CD27−CD10−CD21hi) were also sorted and used as a control for the unselected BCR repertoire. Sample information, including the number of sorted cells and the number of sequencing reads, is listed in Table II.

TABLE II

BCR sequencing summary

| Sample | HCV Status | Time Point Tested (Estimated) | Sorted Cells | Sorted Cell Number | Productive Sequences Total | Productive Sequences Unique | Clonality |
|---|---|---|---|---|---|---|---|
| HCV-8 | Chronic | 5 y | Naive B cells[a] | 40,000 | 414,673 | 9611 | 0.037 |
|  |  |  | HCV E2-specific B cells[b] | 250 | 4643 | 32 | 0.355 |
| HCV-9 | Chronic | 6 y | Naive B cells | 40,000 | 996,999 | 11,927 | 0.029 |
|  |  |  | HCV E2-specific B cells | 220 | 10,814 | 62 | 0.089 |

[a]Naive B cells are CD19$^+$CD27$^-$CD10$^-$CD21$^{hi}$.
[b]HCV E2-specific B cells are class-switched memory B cells (CD19$^+$CD27$^+$IgM$^-$).

Figure 5:
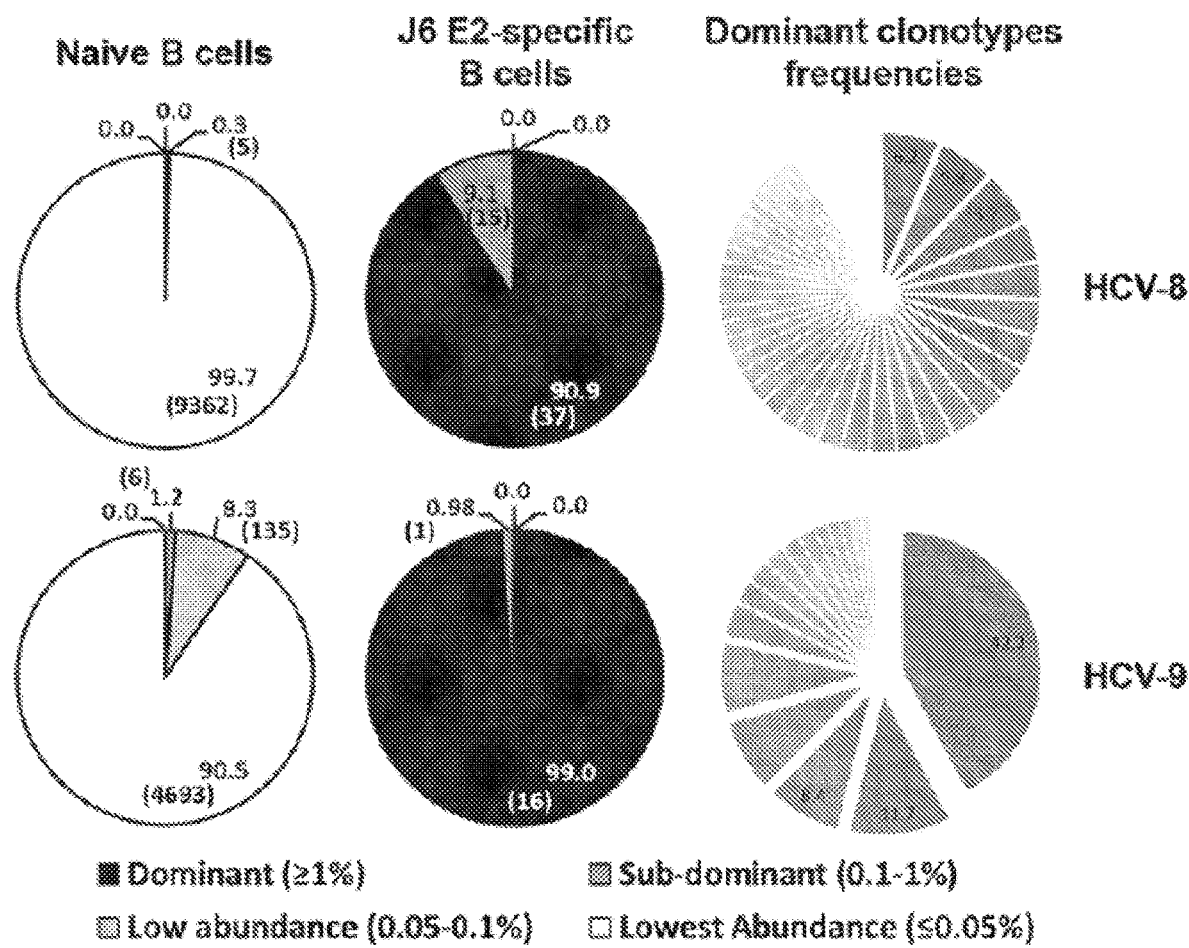
FIG. 5 shows dominance profiles of BCR repertoires from HCV E2-specific and naive B cells. Naive B cells (CD19+CD27−CD10−CD21hi) and J6-E2 tetramer-specific class-switched B cells (CD19+CD27+IgM−) from two HCV chronic subjects (HCV-8 [top] and HCV-9 [bottom]) were sorted and BCR H chain (IGH) deep sequenced as described in Materials and Methods. Unique sequences (clonotypes) were stratified into four groups according to their frequency within the repertoire: dominant clonotypes (black, frequency>1%); subdominant clonotypes (dark gray, frequency 0.1-1%); low abundance clonotypes (light gray; frequency 0.05-0.1%); lowest abundance clonotypes (white; frequency<0.05%). The percentage of each category is indicated in the pie charts and the numbers in brackets represent the number of unique clonotypes forming each category. The frequencies of individual clonotypes within the dominant category (HCV E2-specific samples) are shown in the subdivided pie charts on the right.

The resulting list of unique clonotypes were divided into four groups based on their frequency within the repertoire: 1) dominant clonotypes each representing >1% of the repertoire, 2) subdominant clonotypes representing 0.1-1% of the repertoire, 3) low abundance clonotypes representing 0.05-0.1% of the repertoire, and 4) lowest abundance clonotypes, with frequencies of <0.05% of the repertoire. As expected, the BCR repertoire of naive B cells showed no selection of dominant clonotypes and very few subdominant clonotypes (FIG. 5, left pie charts). For both subjects, most of the naive repertoire (>90%) was composed of the lowest abundance clonotypes. In sharp contrast, the repertoire of HCV E2-specific tetramer positive class-switched memory B cells was focused in both subjects where most of the clonotypes identified (90-99%) were dominant (FIG. 5, middle pie charts). Participant HCV-9 possessed 16 clonotypes totaling 99% of the B cell repertoire, whereas the repertoire of participant HCV-8 was composed of 37 clonotypes, totaling 90% of the total repertoire. The most dominant clonotype for participant HCV-9 (IGHV03-D05-J06-01) represented 42% of the repertoire, whereas the most dominant clonotype for participant HCV-8 (IGHV04-D02-02J05-01) represented only 6% of the repertoire (FIG. 5, right pie charts). Together, these results demonstrate that the J6-E2 tetramer can be used to identify, select, and sort HCV-specific B cells for downstream analyses. Further, the focused repertoire from both HCV-infected subjects suggest Ag-specific selection and/or expansion of this B cell population.

Figure 6A:
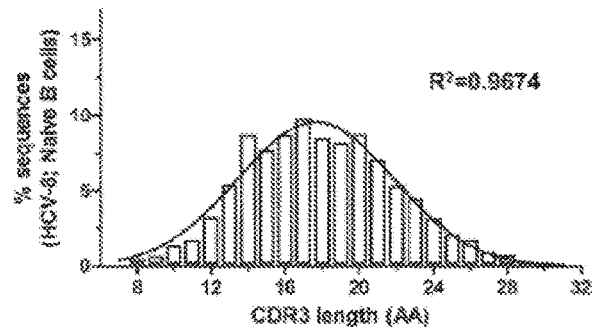
FIG. 6A shows CDR3 length distributions and increased mutation frequency in the HCV E2-specific BCR repertoire as compared with naive B cells. Distribution of amino acid (AA) lengths of CDR3 regions presented as percentage of sequences from the total repertoire. Naive B cell samples from HCV-8 (A) subjects showed a normal Gaussian-like distribution.
Figure 6B:
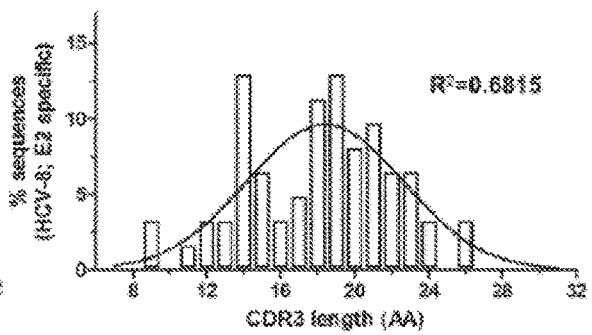
FIG. 6B shows HCV E2-specific class-switched memory B cells from HCV-8 subjects had a skewed distribution divergent from the Gaussian-like shape.
Figure 6C:
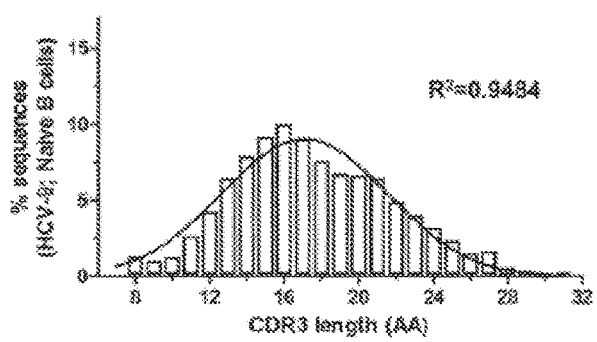
FIG. 6C shows HCV-9 subjects showed a normal Gaussian-like distribution.
Figure 6D:
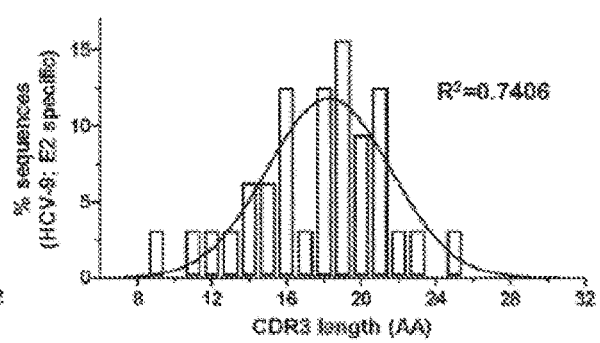
FIG. 6D shows HCV E2-specific class-switched memory B cells from HCV-9 subjects had a skewed distribution divergent from the Gaussian-like shape.

Distinct CDR3 Length Distribution in HCV E2-Specific Class-Switched Memory B Cells Compared with Naive B Cells Profile In a naive B cell repertoire, it is estimated that CDR3 lengths have a normal Gaussian-like distribution with no particular selection or amplification of any clonotype. However, in an Ag-specific population particular clonotypes are selected and go through the process of affinity maturation leading to the enrichment and dominance of certain CDR3 lengths. The distribution of CDR3 lengths for both the naive and E2-specific sorted samples was analyzed. As demonstrated in FIGS. 6A and 6C, the CDR3 lengths within the naive samples showed a normal bell shape distribution in both subjects (R2>0.94). In contrast, the CDR3 length distributions from E2-specific B cells were skewed in both subjects (FIGS. 6B, 6D; R2<0.75). In participant HCV-8, lengths of 14, 18 and 19 aa were highly enriched (FIG. 6B). Likewise, CDR3 lengths of 16 and 18-21 aa were enriched in participant HCV-9 (FIG. 6D). These results provide additional evidence that E2-tetramer positive cells are indeed Ag-specific and have undergone specific selection and expansion during HCV infection.

Figure 6E:
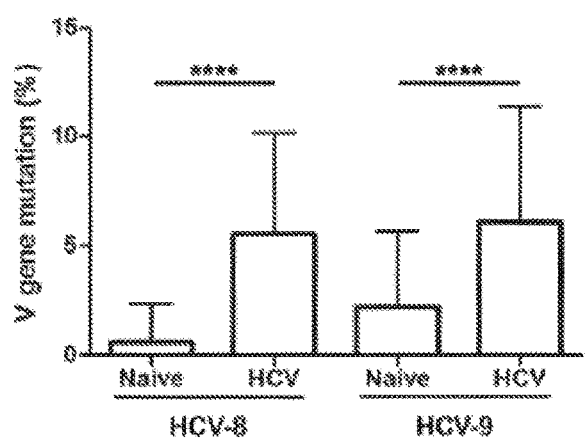
FIG. 6E shows data on mutation frequencies within the V gene segment of CDR3 regions for all samples represented as the number of substitution/100 bp compared with germline sequence according to the IMGT database.

Increased Mutation Frequency in CDR3 Regions from HCV E2-Specific Class-Switched Memory B Cells Compared with Naive B Cells During the process of affinity maturation, the V region of the BCR undergoes somatic hypermutation, followed by selection of clones with the highest affinity to the Ag. There was a statistically significant increase in the V gene mutation frequency from HCV E2-specific samples compared with the corresponding naive B cell samples in both subjects (FIG. 6E). There were no differences in the average mutation frequencies between the HCV E2-specific HCV-8 and HCV-9 samples. This suggests that HCV E2-specific class-switched memory B cells underwent affinity maturation and accumulated a significant number of mutations that were specific for each participant.

What is claimed is:

1. A vector construct useful in expressing biotinylated antigen monomers, said construct comprising:
   a segment encoding a viral protein or functional fragment thereof;
   a segment encoding a biotinylation site inserted downstream of the segment encoding the viral protein or functional fragment thereof,
   wherein the viral protein has the HCV E2 sequence of THTVGGSAAQTTGRLTSLFDMGPRQKIQLVNTNGSWHINRTALNCNDSLHTGFI ASLFYTHSFNSSGCPERMSACRSIEAFRVGWGALQYEDNVTNPEDMRPYCWHYPPRQC GVVSAKTVCGPVYCFTPSPVVVGTTDRLGAPTYTWGENETDVFLLNSTRPPLGSWFGCT WMNSSGYTKTCGAPPCRTRADFNASTDLLCPTDCFRKHPDTTYLKCGSGPWLTPRCLID YPYRLWHYPCTVNYTIFKIRMYVGGVEHRLTAACNFTRGDRCNLEDRDRS (SEQ ID NO: 4), and
   wherein the biotinylation site has the amino acid sequence of GLNDIFEAQKIEWHE (SEQ ID NO: 2).

2. The construct of claim 1 further comprising a segment encoding a signal sequence upstream from the segment encoding the viral protein or functional fragment thereof.

3. The construct of claim 1 further comprising a segment encoding a cleavage site inserted downstream of the segment encoding the viral protein or functional fragment thereof and the segment encoding the biotinylation site.

4. The construct of claim 1 further comprising a segment encoding a tag for affinity purification inserted downstream of the segment encoding the viral protein or functional fragment thereof and the segment encoding the biotinylation site.

5. The construct of claim 1 further comprising a reporter gene inserted downstream of the viral protein or functional fragment thereof and the biotinylation site.

6. The construct of claim 1 wherein the segment encoding the viral protein comprises the ectodomain of Hepatitis C Virus (HCV) envelope glycoprotein E2 or Human Immunodeficiency Virus (HIV) gp140.

7. A vector construct useful in expressing biotinylated antigen monomers, said construct comprising:
   a segment encoding a viral protein or functional fragment thereof;
   a segment encoding a biotinylation site inserted downstream of the segment encoding the viral protein or functional fragment thereof;
   a segment encoding a cleavage site, segment encoding a tag for affinity purification and reporter gene inserted downstream of the segment encoding the viral protein or functional fragment thereof;
   a segment encoding signal sequence upstream from the viral protein or functional fragment thereof;
   wherein the viral protein has the HCV E2 sequence of THTVGGSAAQTTGRLTSLFDMGPRQKIQLVNTNGSWHINRTALNCNDSLHTGFI ASLFYTHSFNSSGCPERMSACRSIEAFRVGWGALQYEDNVTNPEDMRPYCWHYPPRQC GVVSAKTVCGPVYCFTPSPVVVGTTDRLGAPTYTWGENETDVFLLNSTRPPLGSWFGCT WMNSSGYTKTCGAPPCRTRADFNASTDLLCPTDCFRKHPDTTYLKCGSGPWLTPRCLID YPYRLWHYPCTVNYTIFKIRMYVGGVEHRLTAACNFTRGDRCNLEDRDRS (SEQ ID NO: 4); and
   wherein the biotinylation site has the amino acid sequence of GLNDIFEAQKIEWHE (SEQ ID NO: 2).

8. A tetramer comprising a plurality of biotinylated antigen monomers produced from the construct of claim 1.

9. An HCV envelope glycoprotein E2 monomer vector construct, said construct comprising:
   a segment encoding an ectodomain of HCV envelope glycoprotein E2;
   a segment encoding a biotinylation site inserted downstream of the segment encoding the glycoprotein,
   a segment encoding a cleavage site, a segment encoding a tag for affinity purification and a reporter gene inserted downstream of the segment encoding the glycoprotein;
   a segment encoding a signal sequence upstream from the glycoprotein; and
   wherein the viral protein has the HCV E2 sequence of THTVGGSAAQTTGRLTSLFDMGPRQKIQLVNTNGSWHINRTALNCNDSLHTGFIASLFY THSFNSSGCPERMSACRSIEAFRVGWGALQYEDNVTNPEDMRPYCWHYPPRQCGVVSA KTVCGPVYCFTPSPVVVGTTDRLGAPTYTWGENETDVFLLNSTRPPLGSWFGCTWMNS SGYTKTCGAPPCRTRADFNASTDLLCPTDCFRKHPDTTYLKCGSGPWLTPRCLIDYPYR LWHYPCTVNYTIFKIRMYVGGVEHRLTAACNFTRGDRCNLEDRDRS (SEQ ID NO: 4).

10. A tetramer comprising monomer viral proteins having the HCV E2 sequence of
    THTVGGSAAQTTGRLTSLFDMGPRQKIQLVNTNGSWHINRTALNCNDSLHTGFIASLFY THSFNSSGCPERMSACRSIEAFRVGWGALQYEDNVTNPEDMRPYCWHYPPRQCGVVSA KTVCGPVYCFTPSPVVVGTTDRLGAPTYTWGENETDVFLLNSTRPPLGSWFGCTWMNS SGYTKTCGAPPCRTRADFNASTDLLCPTDCFRKHPDTTYLKCGSGPWLTPRCLIDYPYR LWHYPCTVNYTIFKIRMYVGGVEHRLTAACNFTRGDRCNLEDRDRS (SEQ ID NO: 4).

* * * * *